United States Patent [19]

Funakubo et al.

[11] Patent Number: 4,943,296
[45] Date of Patent: Jul. 24, 1990

[54] ROBOT FOR SURGICAL OPERATION

[75] Inventors: Hiroyasu Funakubo; Takeyoshi Dohi, both of Tokyo; Ichiro Sakuma, Akishima; Takashi Komeda, Tokyo, all of Japan

[73] Assignee: Life Technology Research Foundation, Tokyo, Japan

[21] Appl. No.: 285,341

[22] Filed: Dec. 12, 1988

Related U.S. Application Data

[63] Continuation of Ser. No. 35,661, Mar. 26, 1987, abandoned.

[30] Foreign Application Priority Data

Mar. 28, 1986 [JP] Japan .................................. 61-68424
Mar. 25, 1987 [JP] Japan .................................. 62-69086

[51] Int. Cl.$^5$ ............................................. A61B 17/32
[52] U.S. Cl. .......................................... 606/166; 901/8; 901/15
[58] Field of Search .................... 128/303 R, 321, 322, 128/305, 305.1, 310; 901/15, 8; 606/166, 167

[56] References Cited

U.S. PATENT DOCUMENTS

| | | | |
|---|---|---|---|
| 2,838,050 | 6/1958 | Ara ...................... | 128/310 |
| 4,336,805 | 6/1982 | Smirmaul ............... | 128/310 |
| 4,604,016 | 8/1986 | Joyce ..................... | 414/7 |
| 4,712,971 | 12/1987 | Fyler ..................... | 901/23 X |

FOREIGN PATENT DOCUMENTS

| | | | |
|---|---|---|---|
| 2854514 | 9/1979 | Fed. Rep. of Germany | 128/305 |
| 225618 | 8/1985 | German Democratic Rep. | 128/305 |

*Primary Examiner*—Michael H. Thaler
*Attorney, Agent, or Firm*—Lowe, Price, LeBlanc, Becker & Shur

[57] ABSTRACT

A robot for surgical operation which comprises arm structure mounted at its one end of a vertical support and extending in a predetermined direction.

The robot comprises a drive mechanism mounted on the other end of the arm structure and adapted to extend substantially horizontally further in said predetermined direction. A head or trepan is mounted at the extended end of and driven by said drive mechanism. Light transmissive fiber or the like mounted on the trepan takes an image of the patient and a controller process the image through video data processing for driving the arm structure, thereby controlling the position and tilt of the trepan with respect to the patient.

13 Claims, 9 Drawing Sheets

ROBOT FOR SURGICAL OPERATION

This application is a continuation of application Ser. No. 07/035,661, filed Mar. 26, 1987 now abandoned.

BACKGROUND OF THE INVENTION

1. Field of the Invention

This invention relates to a robot for surgical operation which is utilized in a surgical operation which is conducted under a microscope such as a surgical operation for transplantation of a cornea and a trepan positioning apparatus for the robot.

2. Description of the Prior Art

Conventionally, when a surgical operation for transplantation of a cornea or the like is to be conducted, at first a cornea of a patient must be excised. Such an operation must be conducted using a microscope because an object for excision is very small, and where such a surgical operation is conducted by a surgeon, considerable skill is required.

Thus, it may be recommended to use a robot as an available means. In such a case, however, an excising device for excising a cornea and a driving source for driving the excising device will be located on an axis, and accordingly a problem occurs that a part to be excised cannot actually be excised while using a microscope.

Further, since such a robot has a structure of a cantilever secured to a floor, a play may readily appear between a bed on which a patient lines and the robot. Accordingly, the robot is unsuitable for an operation which requires accurate positioning.

SUMMARY OF THE INVENTION

The present invention contemplates resolution of the conventional problems described above, and it is an object of the invention to provide a robot for surgical operation which can be secured directly to a bed and wherein a driving means for driving a head member by way of an arm means can be moved freely relative to an affected part of a patient and the head member is located at a position spaced away from the driving means to allow the affected part of the patient to be directly observed via the head member by means of a microscope. Another object of the invention is to provide a trepan (a head or mechanical assembly which performs resection of cornea etc.) positioning apparatus for the operator to quickly and accurately position a cutter or the like onto the portion to be resected watching the image of the portion displayed on a TV screen delivered through light conducting materials such as light fibers or vision sensors such as CCD.

BRIEF DESCRIPTION OF THE DRAWINGS

The drawings show an embodiment of a robot for surgical operation according to the present invention.

DETAILED DESCRIPTION OF THE INVENTION

Figure 1:
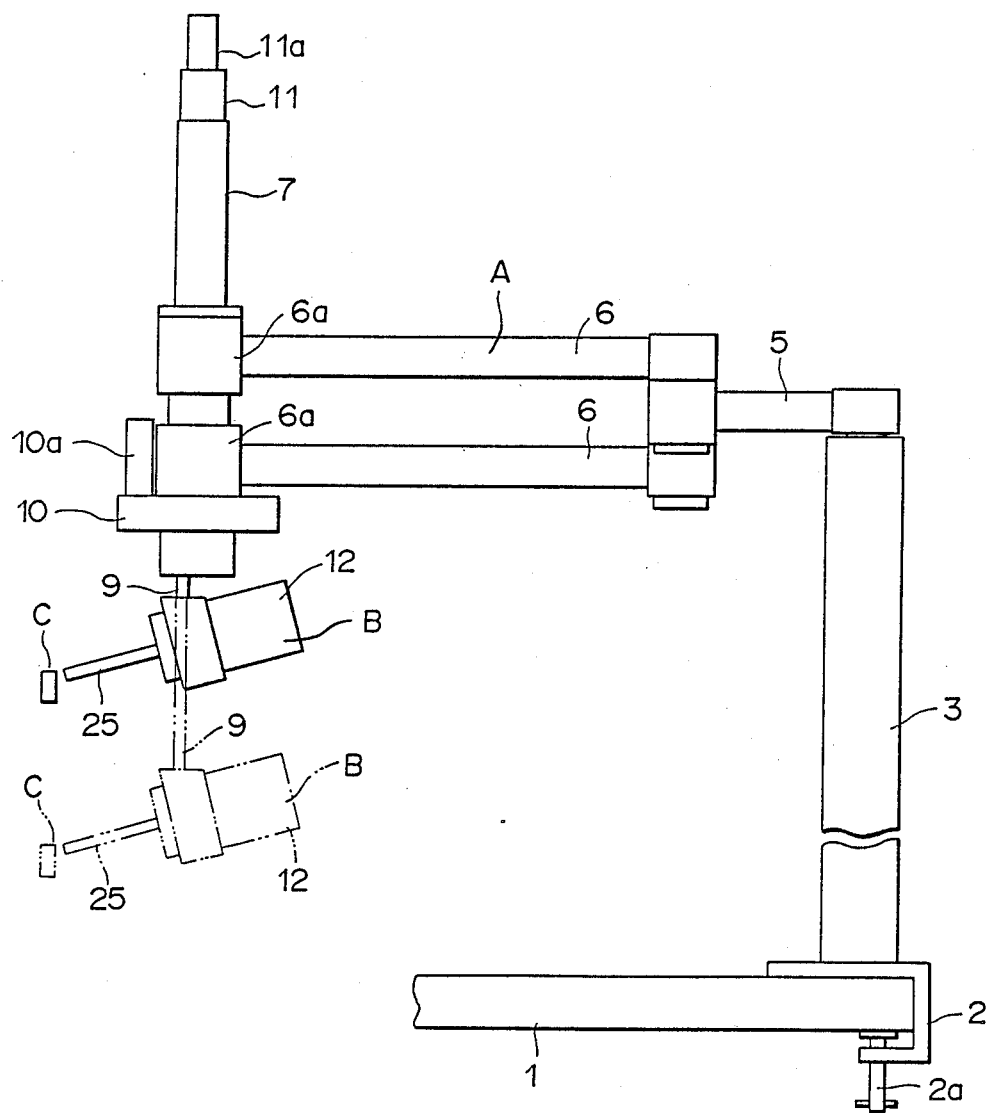
FIG. 1 is a side elevational view of the entire robot.
Figure 2:
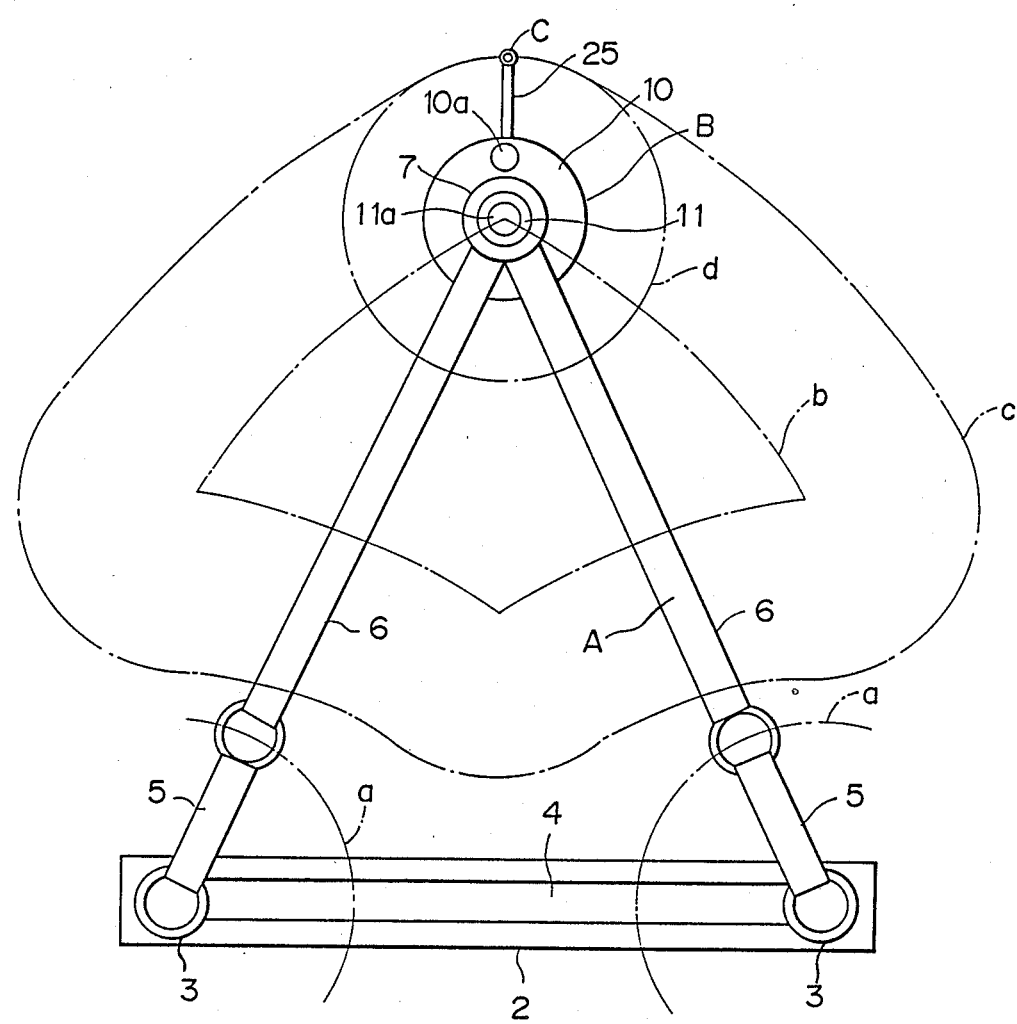
FIG. 2 a plan view of the robot.

Now, an embodiment of the present invention will be described with reference to the drawings. FIG. 1 is a side elevational view of an entire robot, and FIG. 2 is a plan view of the robot of FIG. 1. Referring to FIGS. 1 and 2, reference symbol A denotes an arm means, B a driving means and C a head member. The arm means A has a following structure. Reference numeral 1 denotes a bed on which a patient is to lie, 2 a mounting plate removably mounted on the bed 1 by means of a screw 2a, and 3 a pair of support posts secured to opposite ends of the mounting plate 2 and reinforced by a connecting rod 4 mounted at upper portions thereof. Reference numeral 5 denotes a first arm which is pivoted as indicated by a line a by means of a motor (not shown) embedded at the top end of each of the support posts 3, and 6 a second arm supported for pivotal motion at an end of each of the first arms 5.

An outer tube 7 is supported for rotation on a pair of support tubes 6a securely mounted at ends of the second arms 6. A vertical shaft 9 is fitted for sliding movement in the outer tube 7. Of the two support tubes 6a, the lower support tube 6a has mounted thereon a rotating mechanism 10 which includes a motor 10a for rotating the vertical shaft 9. Mounted at the top end of the outer tube 7 is a vertically moving means 11 which includes a motor 11a for moving the vertical shaft 9 up and down.

Accordingly, the vertical shaft 9 is rotated by the rotating mechanism 10, and the vertical shaft 9 is moved up and down by the vertically moving mechanism 11. The driving means B is mounted at the bottom end of the vertical shaft 9 described above.

Figure 3:
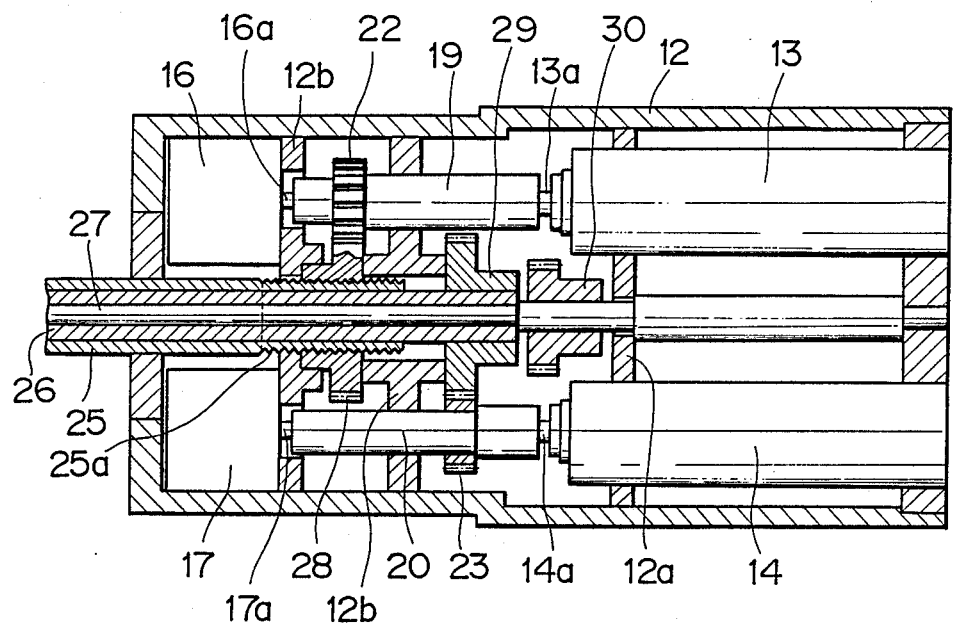
FIGS. 3 and 4 are cross sectional views of a driving means.
Figure 4:
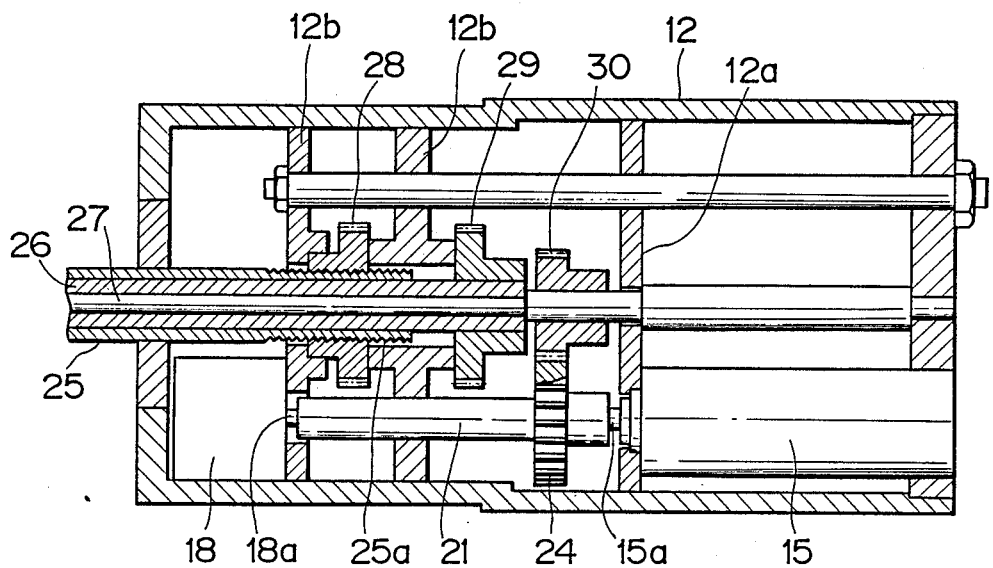
Figure 5:
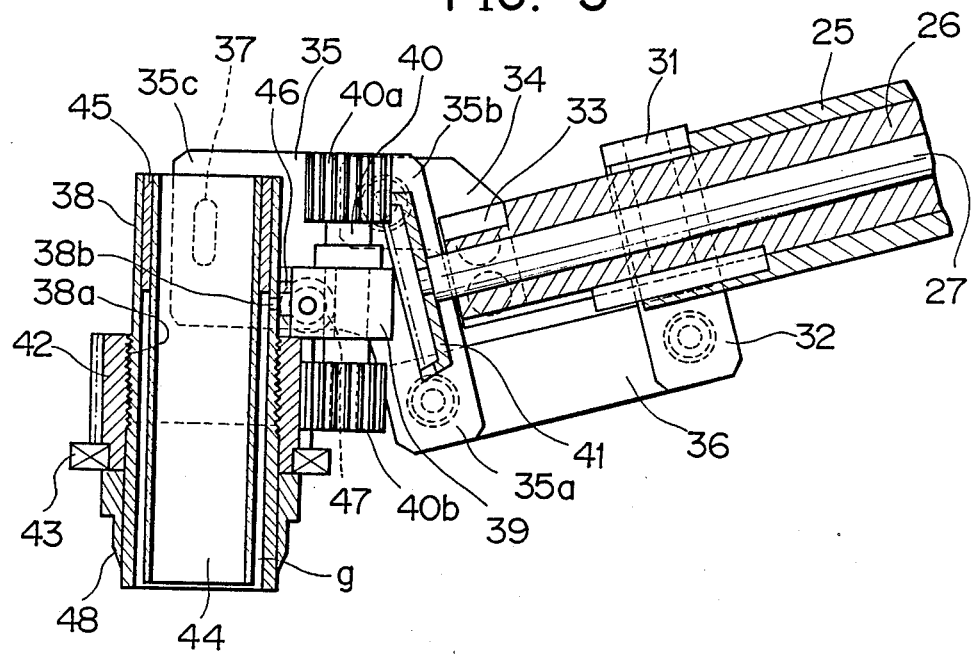
FIG. 5 is a cross sectional view of a head member.

Now, structure of the driving means B will be described with reference to FIGS. 3 and 4.

Reference numeral 12 denotes a casing secured to the bottom end of the vertical shaft 9, and three motors 13 to 15 are secured in a spaced relationship by an angular distance of about 120 degrees from each other to an internal rear half portion of the casing 12.

Shafts 19 to 21 having individual one ends secured to rotary shafts 16a to 18a of encoders 16 to 18 are secured at the other ends thereof to output shafts 13a to 15a of the motors 13 to 15, respectively. Reference numerals 22 to 24 denotes gear wheels secured in a mutually offset relationship from each other to the shafts 19 to 21, respectively. It is to be noted that the shafts 19 to 21 are supported for rotation on two partition plates 12b located within the casing 12.

Reference numeral 25 denotes a moving pipe for rocking the head member C, 26 a rotary pipe for rotating the head member C, and 27 a rotary shaft for rotating a cutter 48 hereinafter described which is removably mounted on the head member C. The rotary shaft 27 is supported at a base end side thereof for rotation on a bearing 12b of the casing 12. The rotary pipe 26 is fitted for rotation on the rotary shaft 27, and the moving pipe 25 is mounted for sliding movement on the rotary pipe 26. It is to be noted that the moving pipe 25 is supported also at the other end of the casing 12.

Reference numeral 28 denotes a connecting gear wheel having a female threaded portion into which a male threaded portion 25a formed at a base portion of the moving pipe 25 is screwed, and the connecting gear wheel 28 is arranged such that it can rotate but is held from movement in a transverse direction by the partition plates 12b. An external toothed gear of the connecting gear wheel 28 is meshed with the gear wheel 22. Accordingly, as the motor 13 rotates, the connecting gear wheel 28 is rotated via the shaft 19 and the gear wheel 22, and consequently the moving pipe 25 which is screwed in the connecting gear wheel 28 is moved in the leftward or rightward direction in FIGS. 3 and 4.

Reference numeral 29 denotes a gear wheel fitted on a base end of the rotary pipe 26 which is exposed from the base end of the moving pipe 25, and the gear wheel 23 is meshed with the gear wheel 29. Reference numeral 30 denotes another gear wheel fitted on a base end of the rotary shaft 27 which is exposed from the base end of the rotary pipe 26, and the gear wheel 24 is meshed with the gear wheel 30.

Accordingly, as the motors 14, 15 rotates, the gear wheels 29, 30 are rotated via the shafts 20, 21 and the gear wheels 23, 24, respectively, and consequently, the rotary pipe 26 and the rotary shaft 27 on which the gear wheels 29, 30 are fitted are rotated, respectively.

The head member C for directly conducting a surgical operation such as an excision of a cornea is connected in this manner to ends of the moving pipe 25, the rotary pipe 26 and the rotary shaft 27 which are moved in leftward and rightward directions or rotated by the motors 13 to 15, respectively.

Now, the head member C will be described with reference to FIGS. 5 to 8.

Reference numeral 31 denotes a fixed plate securely mounted at the end of the moving pipe 25, and a pair of moving plates 32 are secured to opposite ends of the fixed plate 31.

Reference numeral 33 denotes another fixed plate securely mounted at the end of the rotary pipe 26, and a pair of links 34 are secured to opposite ends of the fixed plate 33.

Reference numeral 35 denotes a pair of substantially L-shaped attracting pipe holding plates which have base ends 35a connected to the moving plates 32 via links 36 and bent portions 35b connected to the links 34. An outer attracting pipe 38 is secured to ends 35c of the attracting pipe holding plates 35 via spacers 37. A bearing member 39 is mounted between the attracting pipe holding plates 35, and a shaft 40 having gear wheels 40a, 40b mounted at opposite upper and lower ends thereof is supported for rotation on the bearing member 39.

Reference numeral 41 denotes a crown gear securely mounted at the end of the rotary shaft 27 and meshed with the gear wheel 40a on the shaft 40. It is to be noted that such meshing engagement appears in a plane in which the link 34 and the attracting pipe holding plate 35 are mounted for pivotal motion relative to each other.

Reference numeral 42 denotes a vertically moving gear having internal teeth screwed on a male threaded portion 38a formed on an outer periphery of the outer attracting pipe 38. External teeth of the vertically moving gear 42 is meshed with the other gear wheel 40b on the shaft 40. A magnet 43 is fitted on an outer periphery of a lower end of the vertically moving gear 42.

Reference numeral 44 denotes an inner attracting pipe securely mounted on the outer attracting pipe 38 described above via a spacer 45 in the form of a ring fitted in an upper end of the outer attracting pipe 38. An air gap g is defined between the inner attracting pipe 44 and the outer attracting pipe 38 except the spacer 45. A rubber coupling 46 is connected to a small hole 38b formed in the outer attracting pipe 38, and an air pipe 47 is connected to the air gap g via the rubber coupling 46.

Reference numeral 48 denotes a cylindrical cutter which is removably fitted at a lower end of the outer attracting pipe 38 and adapted to be securely attracted to the magnet 43.

Now, operation of the head member C will be described. If the moving pipe 25 is moved in a leftward direction in FIGS. 4 and 5 by the driving means B described above, the attracting pipe holding plates 35 are pivoted around the pivotally connected point thereof to the links 34 via the moving plates 32 and the links 36.

Figure 7:
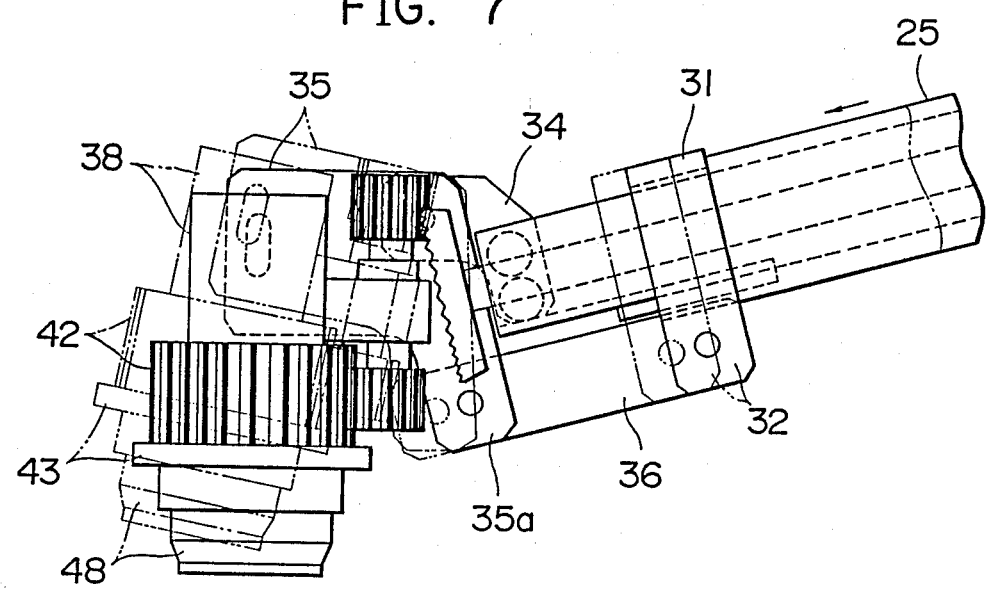
FIG. 7 a side elevational view showing a rocking condition of the head member, and FIG. 8 a side elevational view illustrating upward and downward movement of a cutter of the head member.

Accordingly, the outer attracting tube 38 secured to the attracting pipe holding plate 35 makes a rocking motion as shown in FIG. 7. Consequently, the cutter 48 is naturally caused to make a rocking motion.

In such a rocking motion, the meshing engagement between the crown gear 41 and the gear wheel 40a on the shaft 40 is not influenced at all because the fulcrum of the rocking motion and the meshing position are coincident to each other.

Then, if the rotary pipe 26 is rotated by the driving means B described above, such rotation is transmitted to the outer attracting cylinder 38 via the fixed plate 33 secured to the rotary pipe 26, the link 34s and the attracting pipe holding plates 35 so that the outer attracting tube 38 makes an oscillating motion. It is to be noted that although in this instance the moving plate 25 is also rotated because a turning force acts also upon the fixed plate 31 via the links 36, no influence is had on the cutter 8 because such an oscillating motion is actually effected for positioning before a surgical operation.

Figure 8:
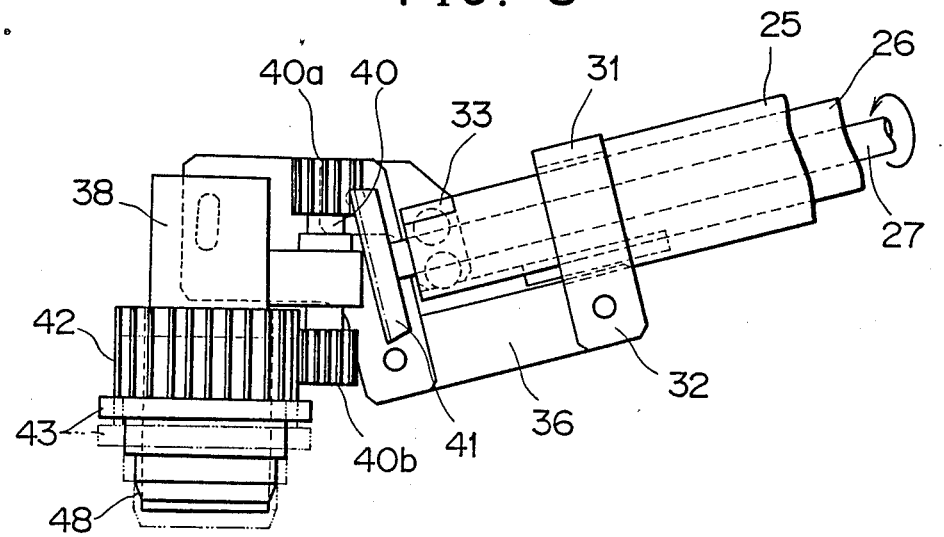
Figure 6:
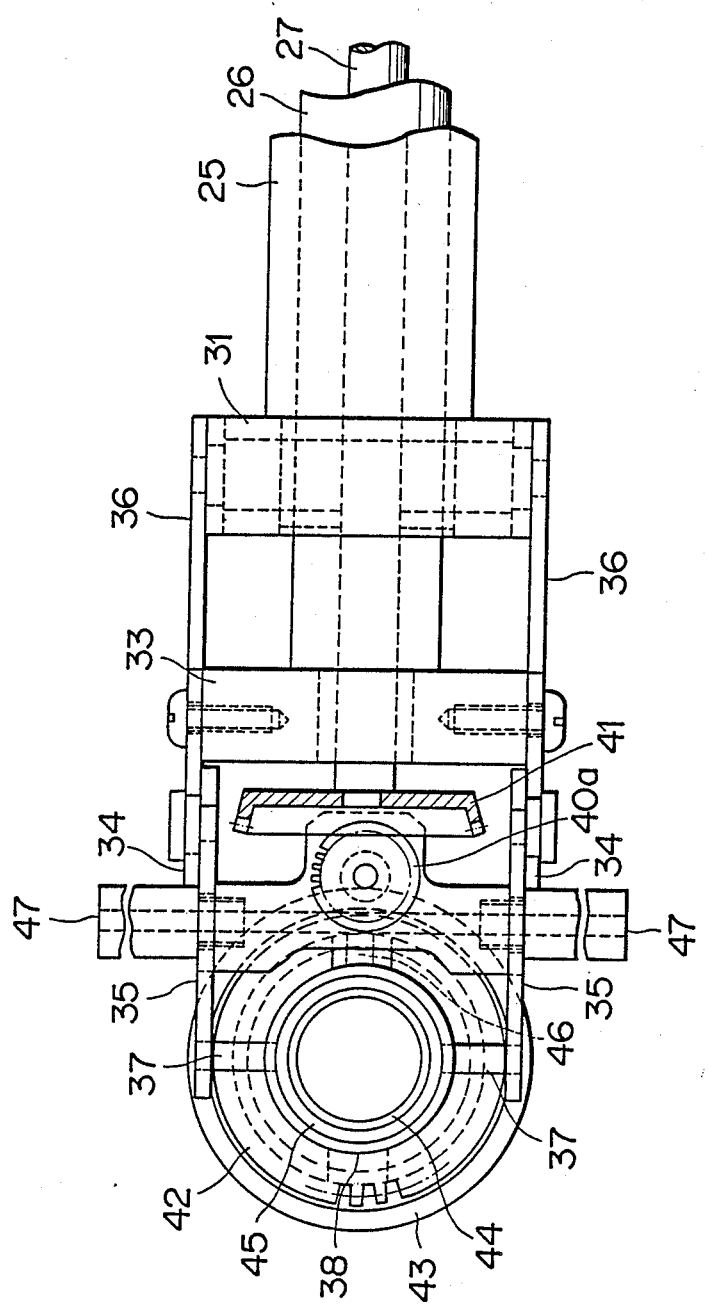
FIG. 6 a plan view of the head member.

Then, if the rotary shaft 27 is rotated by the driving means B described above, a turning force is transmitted to the vertically moving gear 42 via the crown gear 41 and the gear wheels 40a, 40b. Here, if the vertically moving gear 42 is rotated, such rotation of the vertically moving gear 42 involves movement thereof either in an upward direction or in a downward direction due to the specified relationship thereof with the outer attracting tube 38 of the male threaded portion 38a. Accordingly, the cutter 48 secured to the vertically moving gear 42 via the magnet 43 is moved up or down while being rotated as shown in FIG. 8.

Now, description will be given of transplantation of a cornea using the robot according to the present invention.

At first, the robot of the invention is installed adjacent the head side of the bed 1 utilizing the mounting plate 2 of the arm means A. Then, a patient is laid down on the bed 1, and the head of the patient is secured with his or her face located substantially directly below the head member C, and then an eyelid of the patient is secured in an open state by a suitable means.

Subsequently, the motor embedded in the support post 3 is energized to pivot the first arms 5. In this instance, the first arms 5 are pivoted as indicated by the lines a, and accordingly the driving means B is moved inside of another line b while the head member C is moved as indicated by a further line c. Further, the motor 10a is energized to move the head member C as indicated by a still further line d. In this manner, the motor is energized to move the head member C to a position above one of the eyes of the patient from which the cornea is to be excised. Subsequently, the motor 11a is energized to lower the driving device B until the head member C comes to a position near the eye.

With the steps of operation described above, preparations for the first stage have been completed, and subsequently an actual surgical operation is initiated.

At first, air is supplied from the air pipe 47 and delivered toward the eye from the gap g, and while measuring the distance to the eye using an air micrometer (pressure sensor), the motor 11a is energized again to lower the head member C until it is contacted with the eye. Then, when such measurement of the distance finds out a distance by which the head member C is contacted with the eye, the lowering movement of the head member C is stopped. Subsequently, while the eye is being observed from above the inner attracting pipe 44 with the microscope, the motors 13, 14 of the driving device B are energized to cause the head member C to make a rocking motion and an oscillating motion so that the cutter 48 may be positioned just above the cornea.

Then, after completion of such positioning, the motor 15 is energized to rotate the cutter 48 while air within the air gap g is being sucked via the air pipe 47. Accordingly, since the cutter is lowered while being rotated, the cornea is excised while being attracted by the air gap g. Such an excising operation is conducted while a torque applied to the cutter 48 is being measured by way of electric currents through the encoder and the motor. Then, because the torque applied to the cutter 48 decreases just before completion of the intended excision of the cornea, the measuring means detects this so that energization of the motor 15 is interrupted immediately to stop rotation and lowering movement of the cutter 48. Besides, because in this instance the cornea is attracted by the air gap g as described hereinabove, the cornea thus excised is taken out thereby.

Accordingly, the motor 11a is here energized again to rotate in the opposite direction to lift the driving means B, thereby completing the surgical operation for cornea excision.

It is to be noted that while the embodiment is described in connection with excision of a cornea, it can naturally be used for any surgical operation which is conducted under a microscope.

As apparent from the foregoing description, according to the present invention, a robot for surgical operation is constituted such that it can be secured to a bed, that a surgical operating member such as a cutter can be moved freely in vertical and horizontal directions relative to the bed, that the surgical operating member can be rotated to at least allow an affected part to be excised thereby, and that a driving source such as a motor for driving the surgical operating member is located at a horizontal position spaced away from the surgical operating member. Accordingly, a surgical operation can be conducted while an affected part is being observed through the surgical operating member with a microscope. Accordingly, the present invention presents an effect that a surgical operation can be conducted rapidly with accuracy without such skill as required with conventional robots.

The embodiment of a trepan positioning apparatus will now be described as follows. A trepan is the head previously described and is a mechanical assembly which performs resection of a cornea etc..

Figure 9:
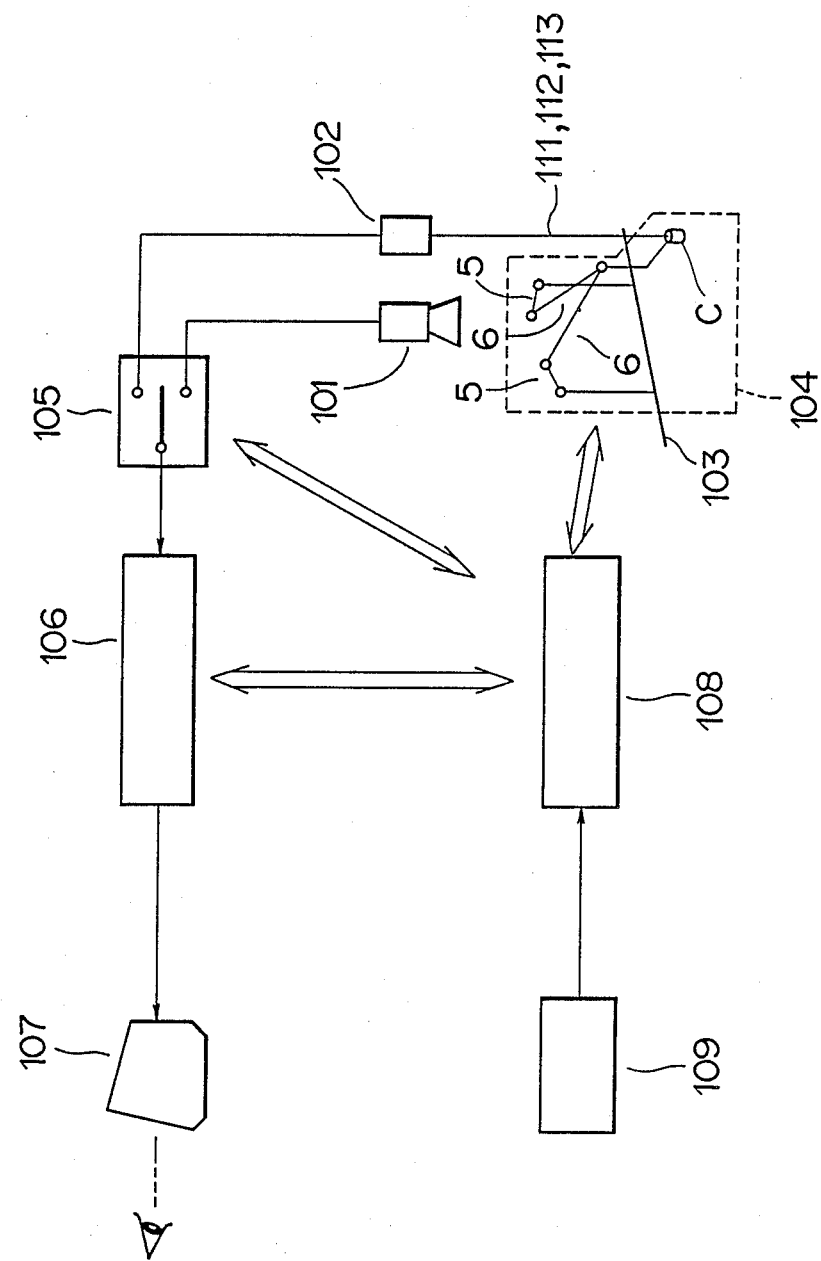
FIG. 9 shows a general configuration of the present apparatus.

FIG. 9 shows a general configuration of the present apparatus. Thick bidirectional arrows denote transmit and receive of control signals between respective untils. The numeral 104 is a robot fixed beside the bed 103 of a patient and controlled by a trepan positioning apparatus according to the present invention.

The numeral 101 is a first TV camera and the numeral 102 a second TV camera. The first TV camera takes the image of whole arms of the robot in a long short thereby measuring the position of the robot arm with respect to the patient.

Watching the TV monitor screen the operator switches the first TV camera and the second TV camera alternately while he operates the apparatus to move the trepan above the cornea of the patient.

A light guide 111 for lighting the cornea and an objective mounted at one end of an image fiber bundle 113 are inserted through the central longitudinal hole of the inner attracting pipe 44 and the second TV camera 102 is connected at the other end of the image fiber bundle 113.

And therefore the position of the cornea with respect to the trepan, when the trepan C is above, is much more accurately determined than the first TV camera 101 does.

At least three tilt detectors such as air micrometers are provided, within the gap g, near the ends of the attracting pipes 38 and 44 opposite to the patient.

The tilt detectors are disposed so that their locations define a triangle or a polygon in a plane normal to the axis of sighting of the objective 112.

And the degree of tilt of the attracting pipes 38 and 44 with respect to the cornea surface can be detected by measuring the location or the distance of the detectors from the cornea surface.

The output signal of the tilt detectors are output to a microcomputer 108 as a controller.

The video signal from the above two TV cameras are displayed on the TV monitor 107 after it is digitalized and stored in a frame memory 106.

The microcomputer 108 determines the center of the cornea through video data processing, which will be discussed later.

Figure 12:
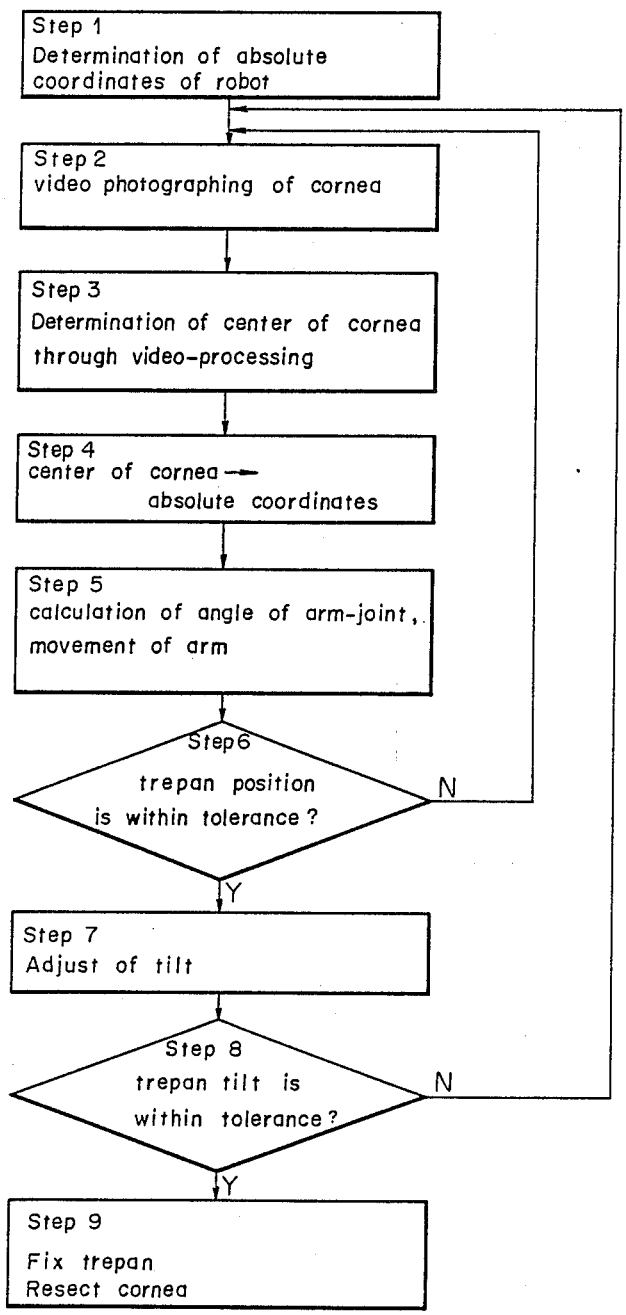
FIG. 12 shows a brief flow chart for illustrating the operation of the present apparatus.

A procedure of cornea resection using the present apparatus will now be discussed referring to FIG. 12.

The operator proceeds the following procedure step by step manually.

STEP 1

Origin of the absolute coordinates of the trepan C is defined at the initial position of the trepan C with respect to the patient. Then the position of the trepan C thereafter will be stored in the controller in accordance with the movements of the arms of robot 104.

STEP 2

The operator knows the approximate position of the patient relative to the robot by watching the picture on the TV monitor 107 from the first TV camera and he positions the trepan C so that the whole cornea is at the center of the image brought by the second TV camera 102.

STEP 3

The microcomputer determines the center of the cornea by video data processing, which will be discussed later, and thereby determining the relative position of the cornea with respect to the present position of the trepan C.

STEP 4

The position of the center of the cornea in the image displayed is translated in to absolute coordinates.

STEP 5

The new angles of respective arm joints of the robot is calculated on the basis of the absolute coordinates obtained in STEP 4 and then the arms of the robot are controlled their movements in accordance with the new angles for moving the trepan C.

STEP 6

The above STEP 2 to STEP 5 are repeated several times till the position of the center of the cornea is within a tolerable range with respect to the trepan C and then the position of the arms of the robot is fixed.

STEP 7

The trepan C descends close to the cornea surface and the attracting pipes 38 and 44 are swang back and forth and left and right so that the central longitudinal axis of the trepan is normal to the spherical surface of the cornea.

STEP 8

The STEP 2 to STEP 7 are repeated to eliminate the deviation of the trepan C from the center of the cornea resulting from STEP 7.

STEP 9

The cornea is fixed firmly at the bottom of the trepan C through suction and is resected.

The video data processing for determining the center of the cornea will now be discussed below.

(1) A method which is carried out manually by an operator.

Figure 10:
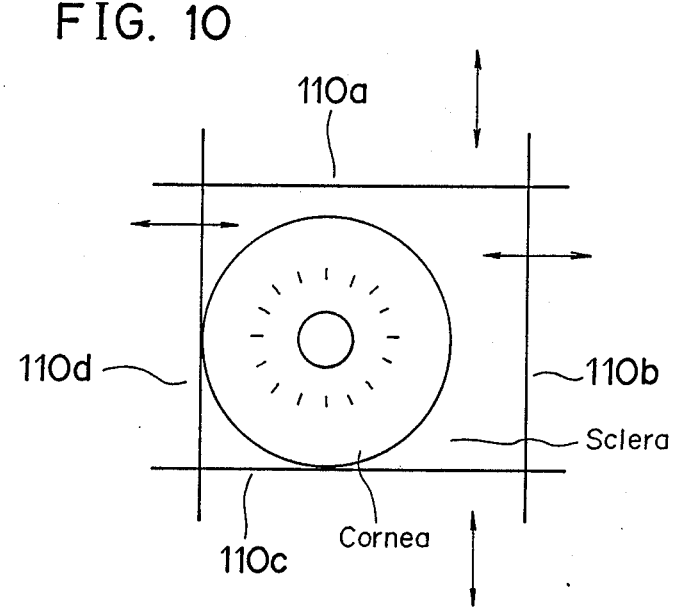
FIG. 10 shows a method for determining the center of a cornea manually.

Four cursors 110a to 110d perpendicular to each other are displayed, under control of microcomputer 108, on the monitor 107 in superposition to the image taken by the second TV camera 102 as shown in FIG. 10.

These cursors are adapted to be moved individually by operating a joy stick or the like. The arrows indicate the direction of movement of the cursors.

The cursors 110a to 110d are positioned at the boundaries between the cornea and sclera in such a way that they form a rectangular which is tangent to the circular cornea. Each cursor is assigned coordinate with respect to the trepan C. When the cursors are moved, the cursors are assigned new coordinates accordingly and the microcomputer 108 determines the position of the center of the cornea on the basis of the new coordinates.

(2) A method which is carried semiautomatically by detecting the boundary between the cornea and sclera through video data processing.

Figure 11A:
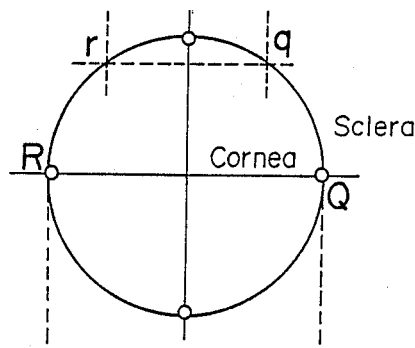
FIG. 11 shows a method for determining the center of a cornea semiautomatically.
Figure 11B:
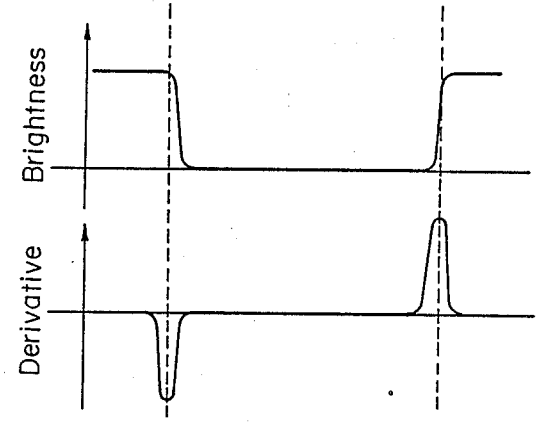
Figure 11C:
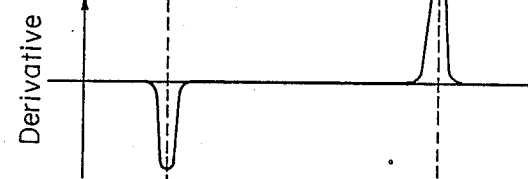
Figure 11D:
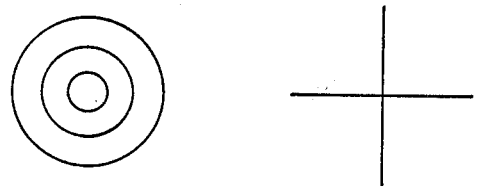

An arithmetic operation for differentiating the brightness of the image is performed by the microcomputer 108 after emphasizing the contrast of the image from the second TV camera as shown in FIG. 11b and the boundary between the cornea and the sclera are detected as shown in FIG. 11c.

The center of the cornea is supposed to exist on a line between boundary points R and Q.

FIG. 11b and FIG. 11c correspond to FIG. 11a in which the boundary points R and Q define a diameter.

The center of the cornea can also be detected on the basis of arbitrary boundary points r and q at the expense of slightly less accuracy.

The center of the cornea is supposed to exist on a line passing through the mid point of points r and q and perpendicular to a line between the points r and q.

Concentric circles and/or a cross shaped cursor can be displayed in superposition to the image on the TV monitor 107 so that the operator is able to comfirm the alignment of the trepan and the cornea by his eyes.

These cursors are electronically stored in the controller and are called on the TV screen by the operator whenever it is necessary.

These cursors can also be applied to the aforementioned manual method for confirming the center of the cornea.

An operator can perform operation watching the cornea directly under a cutter through image fiber bundle which is positioned at the center of the circular cutter rather than looking at, in oblique direction, front edge of the cutter with his eyes.

Therefore it is possible to avoid unwanted injury to the tissue around due to inaccurate positioning of the cutter edge, which results from parallax and so on. It is very convenient in a field, such as cornea transplanting, where it is difficult to obtain alternatives if the resection fails.

What is claimed is:

1. A robot for surgical operation, comprising:
   (a) two spaced vertical support means;
   (b) two sets of articulated arm means, each said set of arm means being rotatably supported at one end thereof to one of said vertical support means and extending substantially horizontally, each set of said arm means consisting of a first elongate member and a second elongate member pivotally connected to each other to provide said articulation, said two sets of arm means being pivotally connected at the free or distal ends thereof to each other;
   (c) head drive means mounted on an axis extending through said connected free or distal ends of said two sets of articulated arm means, for driving a vertically movable member into vertical translatory motion and into rotational motion about the longitudinal axis thereof; and
   (d) a drive mechanism mounted to the lower end of said vertically movable member for controllably supporting and driving at an extended extremity thereof a hollow cylindrical head, said drive mechanism comprising
      a moving pipe for supporting and rocking the head,
      a rotary pipe slidably supported within the moving pipe, the head being attached swingably to the rotary pipe attached to controllably swing about the longitudinal axis of the rotary pipe such that rotation of said rotary pipe about the longitudinal axis thereof causes the head to swing about the longitudinal axis of the rotary pipe,
      a hollow cylindrical treatment member rotatably supported by the head to provide a predetermined treatment at a treatment end thereof,
      a rotary shaft slidably and rotatably supported within the rotary pipe and connected to the head to rotate a surface treatment member attached thereto, and a link mechanism for connecting said moving pipe to said head so that longitudinal movement of the moving pipe relative to the rotary pipe causes said head to swing about an axis perpendicular to the longitudinal axis of said moving pipe.

2. A robot for surgical operation as defined in claim 1, wherein said head comprises an inner cylindrical pipe and an outer cylindrical pipe mounted coaxially with said inner cylindrical pipe so that they define an annular cylindrical air gap between then and the gap is closed at its top end, the lower end of said inner cylindrical pipe being slightly recessed from the lower end of the outer cylindrical pipe, and said outer cylindrical pipe having a hole through its wall.

3. A robot for surgical operation as defined in claim 2, wherein:
the hollow cylindrical treatment member has a cutting edge at the treatment end to effect a tissue cutting motion upon rotation thereof; and
means for reducing an air pressure in said annular cylindrical gap, whereby a tissue cut by the cutting edge is held to the annular air gap and is removable by controlled movement of the head.

4. A robot for surgical operation as defined in claim 3, wherein:
the hollow cylindrical treatment member cutting edge is shaped and sized to perform corneal incision on a patient's eye.

5. A robot for surgical operation as defined in claim 1, wherein said inner cylindrical pipe comprises a brightness detecting means inserted through its hollow portion for detecting the brightness of an image of a patient.

6. A robot for surgical operation as defined in claim 1, wherein said robot further comprises a trepan positioning apparatus, comprising:
(A) a brightness detecting means for detecting the brightness of an image of an affected part, said brightness detecting means being provided through the trepan;
(B) a memory means for storing signals from said brightness detecting means;
(C) a video data processing means for processing the signals stored in the memory means;
(D) a monitor means for displaying said signals stored in said memory means;
and the head being controlled in its position with respect to the affected part on the basis of the output signals through video data processing by said video data processing means.

7. A robot for surgical operation as defined in claim 1, wherein said rob further comprises a trepan positioning apparatus comprising:
(A) a brightness detecting means for detecting the brightness of the image of the affected part, said brightness detecting means being provided through the trepan;
(B) a memory means for storing signals from said brightness detecting means;
(C) a video data processing means for processing the signals stored in said memory means;
(D) a monitor means for displaying said signals stored in the memory means;
(E) a tilt detecting means mounted near the front end of the trepan for detecting that the axis of sighting of the brightness detecting means is normal a surface of the affected part;
and the head being controlled in its position with respect to the affected part on the basis of the results of video data processing by said video data processing means and the output of said tile detecting means.

8. A robot for surgical operation as defined in claim 7, wherein said tilt detecting means are air micrometers.

9. A robot for surgical operation as defined in any one of claim 6 to claim 8, wherein said head drive means is manually controlled by an operator on the basis of the output signals from said tilt detecting means, controlling signals through video data processing by said video data processing means, and a display displayed on said monitor means.

10. A robot for surgical operation as defined in any one of claim 6 to claim 8, wherein said head drive means is automatically controlled on the basis of the output signals from said tilt detecting means, controlling signals through video data processing by said video data processing means.

11. A robot for surgical operation as defined in claim 10, wherein said brightness detecting means comprise a light guiding material.

12. A robot for surgical operation as defined in claim 10, wherein said brightness detecting means comprises a CCD.

13. A robot for surgical operation as defined in claim 1, wherein:
the hollow cylindrical treatment member has a cutting edge at the treatment end to effect a tissue cutting motion upon rotation thereof.

* * * * *